(12) United States Patent
Guo et al.

(10) Patent No.: US 7,759,362 B2
(45) Date of Patent: Jul. 20, 2010

(54) QUINOLONECARBOXYLIC ACID COMPOUNDS, PREPARATION METHODS AND PHARMACEUTICAL USES THEREOF

(75) Inventors: Huiyuan Guo, Beijing (CN); Jiuyu Liu, Beijing (CN)

(73) Assignees: Institut of Medicinal Biotechnology Chinese Academy of Medical Sciences, Beijing (CN); Xinchang Pharmaceutical Factory, Zhejiang Medicine Co. Ltd., Zhejiang (CN)

( * ) Notice: Subject to any disclaimer, the term of this patent is extended or adjusted under 35 U.S.C. 154(b) by 780 days.

(21) Appl. No.: 11/578,828

(22) PCT Filed: Apr. 13, 2005

(86) PCT No.: PCT/CN2005/000489
§ 371 (c)(1),
(2), (4) Date: Oct. 18, 2006

(87) PCT Pub. No.: WO2005/103048
PCT Pub. Date: Mar. 11, 2005

(65) Prior Publication Data
US 2007/0219231 A1     Sep. 20, 2007

(30) Foreign Application Priority Data
Apr. 21, 2004   (CN) .................. 2004 1 0033956

(51) Int. Cl.
C07D 215/38   (2006.01)
A61K 31/48    (2006.01)

(52) U.S. Cl. .................. 514/312; 546/156

(58) Field of Classification Search .......... 543/113, 543/156; 514/312
See application file for complete search history.

(56) References Cited

U.S. PATENT DOCUMENTS 6,114,531 A    9/2000   Norris
6,323,213 B1   11/2001  Bartel et al.
6,432,948 B1    8/2002  Matzke
6,835,848 B1   12/2004  Bose et al.
7,115,744 B2 * 10/2006  Gehring et al. ............. 546/113

FOREIGN PATENT DOCUMENTS

| CA | 2086914 A | 7/1993 |
| CN | 1074218 A | 7/1993 |
| CN | 1211984 A | 3/1999 |
| CN | 1245428 A | 2/2000 |
| CN | 1247865 A | 3/2000 |
| CN | 1427815 A | 7/2003 |
| CN | 1431189   | 7/2003 |
| EP | 0550903   | 7/1993 |
| WO | WO 0145679 | 6/2001 |

OTHER PUBLICATIONS

International Search Report mailed Aug. 4, 2005, for international patent application No. PCT/CN2005/000489 filed Apr. 13, 2005, 4 pages.
Toshihiko et al. (1996). "Studies on Quinolone Antibacterials. IV. Structure-Activity Relationships of Antibacterial Activity and Side Effects for 5- or 8-Substituted and 5,8- Disubstituted-7-(3-amino-1-pyrrolidiny 1)-1-cyclopropyl-1,4-dihydro-4-oxoquinoline-3-carboxylic Acids," *Chemical and Pharmaceutical Bulletin*, 44(5):1074-1085.
Supplemental European Search Report mailed Aug. 11, 2009, for EP application No. 05741956, filed Apr. 13, 2005.

* cited by examiner

*Primary Examiner*—D. Margaret Seaman
(74) *Attorney, Agent, or Firm*—Morrison & Foerster LLP

(57) ABSTRACT

This invention discloses novel quinolonecarboxylic acid derivatives, pharmaceutically acceptable salts or hydrates thereof, and their preparation methods and medical uses. The compounds in this invention show potent antibacterial activity against broad-spectrum pathogenic bacteria, with favorable pharmacokinetics and very low toxicity. The quinolinecarboxylic acid derivatives, which possess a hydrogen atom or an amino group at C-5 position, cis-substituted optical or racemic 2,8-diazo-dicyclo[4,3,0]nonanyl at C-7 position, and difluoromethoxyl at C-8 position of quinolone core, have superior activity against gram-positive bacteria and broad spectrum antibacterial activity compared with the known quinolones.

20 Claims, No Drawings

QUINOLONECARBOXYLIC ACID COMPOUNDS, PREPARATION METHODS AND PHARMACEUTICAL USES THEREOF

CROSS REFERENCE TO RELATED APPLICATIONS

This application is a U.S. national phase application of International Application No. PCT/CN2005/000489, filed Apr. 13, 2005, which claims priority to China Patent Application No. CN 200410033956.8, filed Apr. 21, 2004, the contents of which are hereby incorporated by reference into the present disclosure in their entirety.

FIELD OF THE INVENTION

The present invention relates to quinolonecarboxylic acid compounds, their salts and hydrates, preparation methods thereof, and antibacterial drug compositions containing the same.

BACKGROUND OF THE INVENTION

Quinolones are broad-spectrum, high performance and low toxicity synthetic drugs. Early quinolones have potent activity against gram-negative bacteria, but inferior activity against gram-positive bacteria. Although newly available quinolones such as gatifloxacin (Drug, 1999, 58(4):683) and moxifloxacin (World Notes on Antibiotics, 2002, 23(6):274) exhibit improved antibacterial activity, the activity against gram-positive bacteria, and certain bacteria such as *S. pneumoniae, enterococcus*, etc., needs to be further strengthened. With introduction of difluoromethoxy group at C-8 position of quinolone core, T-3811, a novel quinolone with hydrogen atom at C-6 position of quinolone core (Chinese New Drugs Journal, 2002, 11(10):766), which entered phase III clinical trial in 2001, exhibits enhanced in vitro activity against *S. pneumoniae*, even superior to gatifloxacin.

DETAILED DESCRIPTION OF THE INVENTION

Based on the aforementioned prior art, the present invention aims to provide novel quinolonecarboxylic acid compounds, their salts and hydrates.

The compounds, their salts and hydrates show potent in vitro antibacterial activity against broad-spectrum pathogenic bacteria, superior in vitro activity against *S. pneumoniae* compared to gatifloxacin, favorable pharmacokinetics, and low toxicity. The compounds, which possess a hydrogen atom or an amino group at C-5 position, cis-substituted optical or racemic 2,8-diazo-dicyclo[4,3,0]nonanyl at C-7 position, and difluoromethoxyl at C-8 position of quinolone core, have superior activity against gram-positive bacteria and broad spectrum antibacterial activity compared with the known quinolones.

The invention also provides preparation method for the quinolonecarboxylic acid compounds, their salts and hydrates, and antibacterial drug compositions containing the same.

As a solution to the above problem, the technical proposal of the invention is as follows:

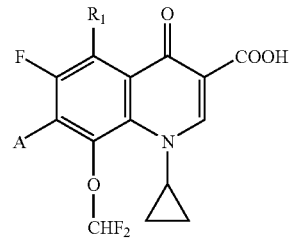

The present invention relates to quinolonecarboxylic acid compounds of formula (I), pharmaceutically acceptable salts or hydrates thereof, wherein $R_1$ is a hydrogen atom or an amino group, A has structure of formula (II) with (1S,6S) configuration, structure of formula (III) with (1R,6R) configuration, or structure of formula (IV) with cis-racemic configuration,

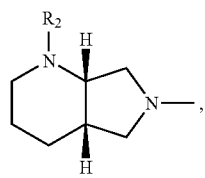

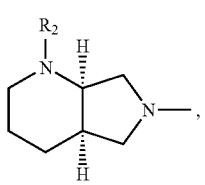

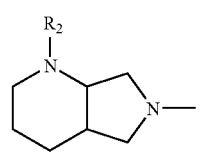

in which $R_2$ is a hydrogen atom or an amino-protecting group.

The amino-protecting group in this invention refers to formyl, acetyl, trifluoroacetyl, benzoyl, paranitrobenzoyl, p-toluene sulfonyl, methoxycarbonyl, ethoxycarbonyl, fluorenyl methoxycarbonyl, t-butyl-oxycarbonyl (BOC) or trichloroethoxycarbonyl.

The salts in this invention are ones of inorganic acids, organic acids or other acids generally known and conventionally applied to quinolone technical field. The salts of inorganic acids can be salt of hydrochloric acid, hydrobromic acid, phosphoric acid, or sulfuric acid. The salts of organic acids can be salt of methanesulfonic acid, p-toluene sulfonic acid, acetic acid, trifluoroacetic acid, lactic acid, citric acid, maleic acid, oxalic acid, succinic acid, benzoic acid, tartaric acid, fumaric acid, mandelic acid, ascorbic acid, or malic acid.

The invention also provides method for preparing compound of formula (I) by reacting compound of formula (V) with compound of formula (VI), wherein $R_1$ is a hydrogen atom or an amino group, $R_3$ is an amino-protecting group, and X is a halogen atom.

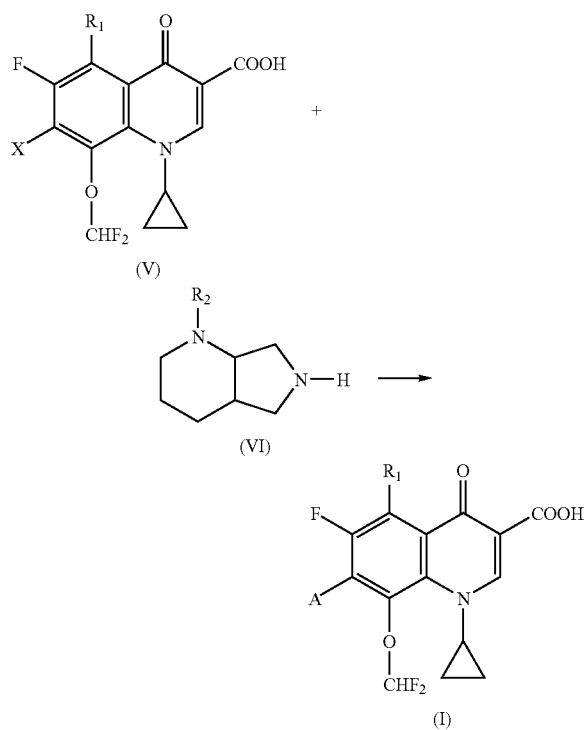

The detailed method comprises reacting compound of formula (V) with compound of formula (VI) in the presence of acid-binding agent under stirring at temperature within room temperature to 200° C. for 1-20 h, and removing amino-protecting group of compound (I), wherein the amino-protecting group can be formyl, acetyl, trifluoroacetyl, benzoyl, paranitrobenzoyl, p-toluene sulfonyl, methoxycarbonyl, ethoxycarbonyl, fluorenyl methoxycarbonyl, t-butyl-oxycarbonyl (BOC) or trichloroethoxycarbonyl, and the halogen atom can be fluorine, chlorine or bromine.

The solvent for the aforementioned reaction can be any solvent having no adverse effect on the reaction, preferably pyridine, acetonitrile, N,N-dimethylformamide, dimethyl sulfoxide, N-methyl pyrrolidone or hexamethyl phosphoramide.

The reaction is commonly carried out in the presence of acid acceptor. In such a case, reactant (VI) is used in excess to increase the reaction efficiency of the relatively expensive starting material (V), for example, molar ratio of compound (VI) to compound (V) is 1-10, preferably 1-5, wherein after the reaction, unreacted compound (VI) can be recovered and reused for another reaction. The acid acceptor is preferably selected from inorganic base, such as sodium bicarbonate, and potassium carbonate, etc., and organic base, such as pyridine, triethyl amine, diisopropylethylamine, N,N-dimethylaniline, N,N-dimethyl aminopyridine, 1,8-diazabicyclo-[5.4.0]undecylene-7-ene and 1,4-diazabicyclo-[2.2.2]octane.

The amino-protecting group of compound (I) can be removed by hydrolysis or solvolysis according to relevant properties of the protecting group. For example, the protecting group can be removed by treating at 0-130° C. in solvent and optionally in the presence of acid or base. The acid useful for this purpose includes inorganic acid, such as hydrochloric acid, hydrobromic acid, sulfuric acid, and phosphoric acid, etc.; organic acid, such as acetic acid, trifluoroacetic acid, formic acid, and toluenesulfonic acid, etc.; or Lewis acid, such as boric tribromide, and aluminum chloride, etc. The base useful for this purpose includes hydroxide of alkali metal or alkaline earth metal, such as sodium hydroxide, and barium hydroxide, etc.; carbonate of alkali metal, such as sodium carbonate, and calcium carbonate, etc.; alkoxide of alkali metal, such as sodium methoxide, and sodium ethoxide, etc. The reaction can be carried out in the presence of solvent, such as water and/or organic solvent including ethanol, tetrahydrofuran, dioxan, ethylene glycol, and acetic acid, etc. If desired, the reaction also can be carried out in absence of any solvent.

The present invention further provides another method for preparing compound of formula (I) by firstly converting compound (VII) into compound (VIII), and then reacting compound (VII) with compound (VI) to obtain compound (I) via intermediate compound (IX),

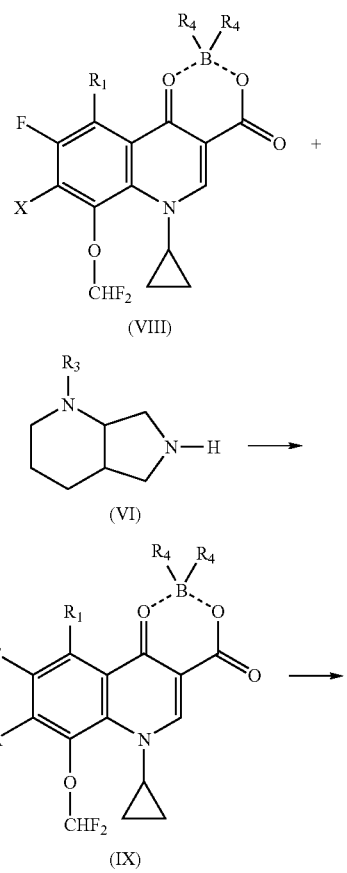

-continued (I)

wherein $R_1$ is a hydrogen atom or an amino group, Y is hydrogen, $C_1$-$C_6$ alkyl, or optionally substituted benzyl, $R_4$ is $C_2$-$C_6$ aliphatic acid group, $C_2$-$C_6$ halogenated aliphatic acid group, or $C_7$-$C_{11}$ aromatic acid group.

And the formula (VI) concerning chiral compound represents three optical isomers possessing (1S,6S) configuration, (1R,6R) configuration, or cis-racemic configuration.

The method specifically comprises reacting compound (VIII) with compound (VI) under stirring in the presence of acid-binding agent for 1-20 h at temperature within room temperature to 200° C. to give compound (IX), and removing boron-containing group and amino-protecting group of the compound (IX).

In the aforementioned scheme, $R_1$, A, $R_3$, and X are as defined above, Y represents H, $C_1$-$C_6$ alkyl, and optionally substituted benzyl; $R_4$ represents $C_2$-$C_6$ aliphatic acid group, $C_2$-$C_6$ halogenated aliphatic acid group, or $C_7$-$C_{11}$ aromatic acid group. The formula (VI) concerning chiral compound represents three optical isomers possessing (1S,6S), or (1R, 6R) configuration or cis-racemic configuration.

Method of converting compound (VII) into compound (VIII) is known, and can be easily realized according to already disclosed method (see EP .0352123). Compound (IX) can be prepared by reacting compound (VIII) with compound (VI) under stirring in the presence of solvent and appropriate amount of base at temperature within room temperature to 200° C. for 1-20 h.

The solvent for the aforementioned reaction can be any solvent having no adverse effect on the reaction, preferably pyridine, acetonitrile, N,N-dimethylformamide, dimethyl sulfoxide, N-methyl pyrrolidone or hexamethyl phosphoramide.

The reaction is commonly carried out in the presence of acid acceptor, In such a case, reactant (VI) is used in excess to increase the reaction efficiency of the relatively expensive starting material (VIII), for example, molar ratio of compound (VI) to compound (VIII) is 1-10, preferably 1-5, wherein after the reaction, unreacted compound (VI) can be recovered and reused for another reaction. The acid acceptor in the reaction is preferably selected from inorganic base, such as sodium bicarbonate, and potassium carbonate, etc., and organic base, such as pyridine, triethyl amine, diisopropylethylamine, N,N-dimethylaniline, N,N-dimethyl aminopyridine, 1,8-diazabicyclo-[5.4.0]undecylene-7-ene and 1,4-diazabicyclo-[2.2.2]octane.

Borate ester moiety of compound (IX) is hydrolyzed while N-deprotection reaction proceeds, thereby generating compound (I).

In the reaction, the amino-protecting group can be removed by hydrolysis or solvolysis according to relevant properties of the protecting group. For example, the protecting group can be removed by treating at 0-130° C. in solvent and optionally in the presence of acid or base. The acid useful for this purpose includes inorganic acid, such as hydrochloric acid, hydrobromic acid, sulfuric acid, and phosphoric acid, etc.; organic acid, such as acetic acid, trifluoroacetic acid, formic acid, and toluenesulfonic acid, etc.; or Lewis acid, such as boric tribromide, and aluminum chloride, etc. The base useful for this purpose includes hydroxide of alkali metal or alkaline earth metal, such as sodium hydroxide, and barium hydroxide, etc.; carbonate of alkali metal, such as sodium carbonate, and calcium carbonate, etc.; alkoxide of alkali metal, such as sodium methoxide, and sodium ethoxide, etc. The reaction can be carried out in presence of solvent, such as water and/or organic solvent including ethanol, tetrahydrofuran, dioxan, ethylene glycol, and acetic acid, etc. If desired, the reaction also can be carried out in absence of any solvent.

The invention further provides a novel method for preparing compound (VII), as is shown in the following scheme 3, in which $R_1$, X and Y are as defined above.

Mixture of halogen acid and acetic acid is generally selected as the reacting agent for converting compound (X) into (XI), preferably mixture of hydrobromic acid

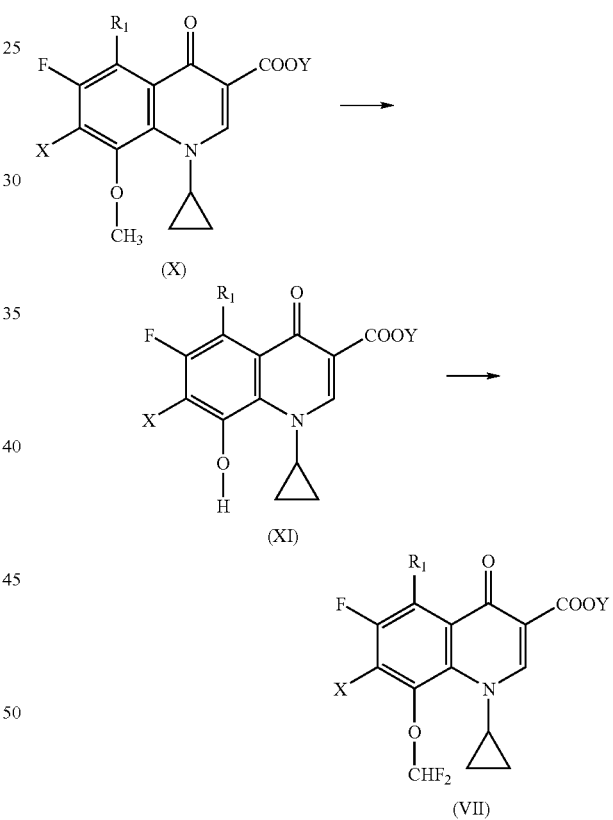

and acetic acid. The molar ratio of hydrobromic acid to compound (X) is 2-20, preferably 4-10, and volume ratio of acetic acid to hydrobromic acid is 1-10, preferably 1-4. The reaction is carried out at 0-120° C., preferably 90-110° C.

The reaction solvent for converting compound (XI) into (VII) can be selected from any solvent having no adverse effect on the reaction, preferably N,N-dimethylformamide, dimethyl sulfoxide, N-methyl pyrrolidone or hexamethyl phosphoramide.

The reaction is generally carried out by reacting compound (XI) with monochlorodifluoromethane in alkaline aqueous solution. The base useful for this purpose includes hydroxide of alkali metal or alkaline earth metal, such as sodium hydroxide, and barium hydroxide, etc.; carbonate of alkaline metal, such as sodium carbonate, and calcium carbonate, etc.; alkoxide of alkaline metal, such as sodium methoxide, and sodium ethoxide, etc.; wherein molar ratio of the base to compound (IX) is 1-5, preferably 2; and molar ratio of monochlorodifluoromethane to the base is 1-50, preferable 10-15.

Starting compound (X) and intermediate compound (XI) in reaction scheme 3 are known compounds (see CN87100580 for compound (X), see *Chinese Journal of Pharmaceuticals* for compound (XI), 2001, 36 (6): 419-422), but interconversion of the compound (X), (XI) and (V) has not been seen in any publication.

By method shown in reaction scheme 4, another starting compound (VI) can be obtained, wherein $R_3$ is as defined above, and $R_5$ represents amino-protecting group, such as optionally substituted benzyl group.

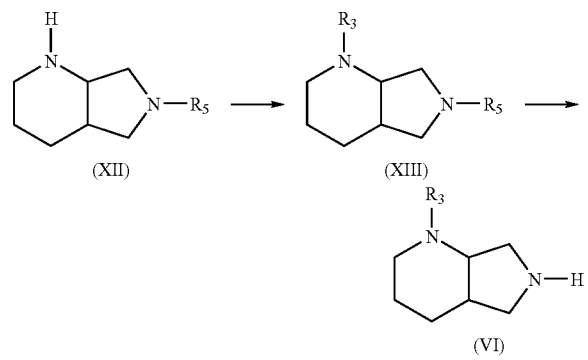

And compounds of formula (XII), (XIII), and (VI) concerning chiral compounds all represent optical isomers possessing (1S,6S), (1R,6R) configuration or cis-racemic configuration.

The aim of converting compound (XII) into compound (XIII) is to introduce amino-protecting group. The protecting group useful for this purpose includes formyl, acetyl, trifluoroacetyl, benzoyl, paranitrobenzoyl, p-toluene sulfonyl, methoxycarbonyl, ethoxycarbonyl, fluorenyl methoxycarbonyl, t-butyl-oxycarbonyl (BOC) or trichloroethoxycarbonyl, etc.

The aim of converting compound (XIII) into compound (VI) is to remove the various benzyl type protecting groups, which can be effectively removed by reduction. Although the reduction conditions for removing the protecting groups vary with the relevant properties of the protecting groups, the reduction is generally carried out in the presence of a catalyst (e.g. Pt, Pa, Raney Ni) in an inert solvent with hydrogen flow at 10-100° C., or with sodium metal or lithium metal and in ammonia water at −50° C. to −10° C., preferably in the presence of 10% Pd/C under 5 atm hydrogen atmosphere at room temperature.

The compound (XII) used as starting material in the reaction scheme 4 is known compound, and can be easily prepared according to the patent: CN 93100215.X A corresponding acid is used in N-deprotection of compound (I) to give corresponding salt.

If desired, the salts of compound (I) can be further dissolved in water or other water-containing organic solvent to form a solution, to which an alkaline aqueous solution or alkaline aqueous organic solvent is added to adjust pH to 6-8, and cooled to separate out hydrate of the compound (I). The base useful for this purpose includes hydroxide of alkali metal or alkaline earth metal, such as sodium hydroxide, and barium hydroxide, etc.; carbonate of alkali metal, such as sodium carbonate, and calcium carbonate, etc.; alkoxide of alkali metal, such as sodium methoxide, and sodium ethoxide, etc.

The present invention also provides drug compositions which contain physiologically effective amount of quinolonecarboxylic acid derivatives 0.1-99.9 wt % and/or pharmaceutically acceptable carrier 0.1-99.9 wt %. The drug compositions exist in the form of pharmaceutically appropriate preparation including tablet, sugar-coated tablet, film-coated tablet, enteric coating tablet, slow release tablet, capsule, hard capsule, soft capsule, slow release capsule, oral liquid, mistura, buccal tablet, granule, pill, pulvis, concentrated extract, bolus, suspensoid, liquor, injection, powder and injection preparation, freeze drying powder and injection preparation, suppositorium, ointment, plaster, cream, spray, aerosol, gutt, and patch.

In a preparation form, the drug compositions in the present invention contain the inventive compound 0.1-1,000 mg per dose as effective quantity, wherein the "dose" means a preparation unit such as a tablet or a capsule, or the administration dosage for each time, for example, 100 mg per time.

When the drug compositions in the present invention are prepared into solid or semisolid pharmaceutical preparation in the form of pulvis, tablet, dispersible pulvis, capsule, cachet, suppositorium or ointment, a solid carrier can be used. The solid carrier useful for this purpose is preferably chosen from one or more of diluent, flavoring agent, solubilizer, lubricant, suspension, binder, and swelling agent; or it can be coating material. In a powder preparation, 5% or 10-70% micronized active ingredient is contained in the carrier. The suitable solid carrier can be selected from magnesium carbonate, magnesium stearate, talcum, sucrose, lactose, pectin, dextrin, starch, gelatin, tragacanth, methyl cellulose, sodium carboxymethylcellulose, low boiling point wax, cocoa butter, etc. Tablet, powder, cachet and capsule are the most favorable preparations for oral administration because they are easy to administrate.

A liquid preparation according to the present invention includes solution, suspension, and emulsion. For example, an injectable preparation for parenteral administration can be in the form of water or water-propylene glycol solution, whose isotonic concentration, pH, etc. are adjusted to fit in vivo physiological conditions. The liquid preparation may also be made into the form of polyethylene glycol or water solution. Aqueous oral liquid can be prepared by dissolving the active ingredient in water, and adding appropriate colorant, flavoring agent, stabilizing agent and thickening agent. Micronized active ingredient can be dispersed in a viscous material, such as natural or synthetic gelatin, methyl cellulose, sodium carboxymethylcellulose or other known suspension to prepare aqueous suspension suitable for oral administration.

For the sake of easy administration and dosage equality, the aforementioned pharmaceutical preparation is preferably formulated into unit dosage form. The "unit dosage form" means the physical separation unit suitable for single dose, and each unit contains the active ingredient in precalculated quantity for realizing anticipated treatment effect. The unit dosage form can be in packaged form, such as tablet, capsule, or powder in a tube or vial, or ointment, gel or cream in a tube or vial.

Although the quantity of the active ingredient contained in each unit dosage form may vary, it is generally adjusted to the range of 1-500 mg according to the efficacy of the selected active ingredient.

When compound of formula (I) in the present invention is used as a drug for treating bacterial infection, the dosage is preferably 6-14 mg/kg body-weight in the first stage. But the dosage may also vary with the need of the patient, seriousness of the infection to be treated, and the compound selected.

Professionals in this field can determine the preferable dosage suitable for a certain situation according to conventional method. Generally, the initial dosage is lower than the optimal dosage of the active ingredient for the treatment, and then the dosage is gradually increased till the optimal treatment effect is realized. For the sake of conveniency, total daily dosage can be divided into several doses for administration.

As is described above, the present compound shows stronger antibacterial activity and broader antibacterial spectrum against various kinds of pathogenic bacteria including gram-negative bacteria and gram-positive bacteria. Compared with the known quinolone antibacterial drugs, such as moxifloxacin, the present compound exhibits stronger antibacterial activity to gram-negative bacteria. Particularly, the activity against gram-positive bacteria of the present compound is much stronger than that of any known quinolones.

The antibacterial activity of the present quinolonecarboxylic acid derivates, in comparison with that of moxifloxacin (of our own make, see *Chinese Journal of Pharmaceuticlas*, 2004, 35(3):129) and ciprofloxacin (provided by Tianjin Central Pharmaceutical Factory, Lot Number 990307) which have been widely used and hold a large market share, is shown in Table 1. The pharmaceutically acceptable salts or hydrates thereof have the same antibacterial activity.

vivo, exhibit extraordinarily high bioavailability, and are suitable as antibacterial agents.

In addition, due to their low toxicity, the present compounds can be effectively used in the prevention and treatment of diseases caused by bacterial infections in homoiotherm including human being.

Acute Oral Toxicity Studies

Toxicity experiments are carried out on the compounds prepared in embodiment 11, 13 and 15 to determine the acute oral toxicity of the present compounds. Solutions of the three compounds in different concentrations are administered to male mice at a dosage of 0.1 mL/10 g body weight, then the number of dead mice after 7 days is recorded, and lethal dose 50% (LD50) is calculated for each compound by Bliss program. The results are summarized in Table 3.

TABLE 3

| Acute oral toxicity of the test compounds in mice | |
| --- | --- |
| Test Compound | LD50/(mg/Kg) |
| Embodiment 13 | >4000 |
| Embodiment 15 | >4000 |
| Embodiment 17 | >4000 |

TABLE 1

| | MIC (g/mL) | | | | | | | |
| --- | --- | --- | --- | --- | --- | --- | --- | --- |
| | Compd. | | | | | | Comparison drugs | |
| Strains | 13 | 14 | 15 | 17 | 18 | 21 | Moxifloxacin | Ciprofloxacin |
| Gram-positive bacteria | | | | | | | | |
| *S. pneumoniae* 98 | 0.015 | 0.015 | 0.125 | 0.015 | 0.125 | 0.03 | 0.125 | 0.25 |
| *S. pneumoniae* 70 | 0.125 | 0.06 | 0.06 | 0.015 | 0.03 | 0.06 | 0.125 | 0.06 |
| *S. pyogenes* 26 | 0.25 | 0.5 | 0.25 | 0.25 | 0.25 | 0.25 | 0.5 | 1 |
| *Enterococcus* 755 | 0.25 | 0.25 | 0.25 | 0.015 | 0.06 | 0.25 | 0.5 | 1 |
| *S. aureus* ATTC 25923 | 0.03 | 0.03 | 0.125 | 0.03 | 0.06 | 0.03 | 0.06 | 0.125 |
| *S. epidermidis* 26069 | 0.25 | 0.5 | 0.5 | 0.25 | 0.25 | 0.25 | 0.5 | 0.5 |
| Gram-negative bacteria | | | | | | | | |
| *E. coli* ATTC 25922 | 0.015 | 0.015 | 0.25 | 0.051 | 0.015 | <0.007 | 0.03 | 0.06 |
| *E. coli* 26 | 0.015 | 0.03 | 0.03 | 0.015 | 0.015 | <0.007 | 0.03 | <0.007 |
| *P. aeruginosa* 17 | 0.25 | 1 | 0.5 | 0.25 | 0.25 | 0.25 | 0.5 | 0.03 |
| *K. pneumoniae* 14 | 0.015 | 0.03 | 0.03 | 0.015 | 0.015 | 0.015 | 0.03 | 0.015 |
| *K. pneumoniae* 7 | 0.015 | 0.03 | 0.03 | 0.015 | 0.015 | 0.015 | 0.03 | 0.015 |

Two-fold plate dilution method is used for determination of activity, with Muener-Hinton medium (DIFCO) as the culture medium and clinically isolated pathogenic strain, quality control strain and standard strain (provided by National Institute for the Control of Pharmaceutical and Biological Products) as test strains.

With respect to pharmacokinetic performance, compared with known quinolones, the present compounds possess proper water solubility so that they can be well absorbed in The results of the experiments show that the three compounds possess low toxicity and are well suited for pharmaceutical uses.

EMBODIMENTS

The following embodiments explain the present invention in further detail, but make no claim to completeness and do not constitute any restriction to the range of the invention.

Referential Example 1

Preparation of 5-Amino-1-cyclopropyl-6,7-difluoro-8-difluoromethoxyl-1,4-dihydro-4-oxoquinoline-3-carboxylic acid The preparation comprises refluxing mixture of reducing iron powder (2.4 g, 42.8 mmol), water (4.5 mL) and acetic acid (0.3 mL) for 15 min under stirring, adding batch-wise ethyl 1-cyclopropyl-6,7-difluoro-8-difluoromethoxyl-5-nitro-1,4-dihydro-4-oxoquinoline-3-carboxylate (4.3 g, 10.6 mmol), adding ethanol (20 mL), continuously refluxing for 6 h under stirring, hot filtering, distilling off the solvent from the filtrate, adding concentrated hydrochloric acid (5 mL) and acetic acid (10 mL) to react at 100° C. for 1 h, cooling to room temperature, filtering, adding ethanol (10 mL) to the filter cake to reflux for 0.5 h, cooling to room temperature, filtering, and drying obtained filter cake to give a pale yellow solid product 5-amino-1-cyclopropyl-6,7-difluoro-8-difluoromethoxyl-1,4-dihydro-4-oxoquinoline-3-carboxylic acid (3.1 g, 84.5%).

$^1$H NMR(DMSO), δ=0.85-1.21(4H, m), 3.89-3.93(1H, m), 7.05(1H, t, J=73.0 Hz), 7.92(2H, br.), 8.62(1H, s), 14.25(1H, s). MS(m/z): 347(M$^+$+1).

Embodiment 1

Preparation of 1-Cyclopropyl-6,7-difluoro-8-hydroxyl-1,4-dihydro-4-oxoquinoline-3-carboxylic acid The preparation comprises dissolving Ethyl 1-cyclopropyl-6,7-difluoro-8-methoxy-1,4-dihydro-4-oxoquinoline-3-carboxylate (10.0 g, 30.9 mmol) in 40% HBr aqueous solution (20 mL) and acetic acid (20 mL) to react at 100° C., charging reaction mixture into ice water (500 mL) under fast stirring after the reaction finishes, going on with the stirring for 0.5 h, filtering, and drying obtained filter cake to give 1-cyclopropyl-6,7-difluoro-8-hydroxy-1,4-dihydro-oxoquinoline-3-carboxylic acid (7.8 g, 89.6%).

$^1$H NMR(DMSO) δ=1.01-1.27(4H, m), 4.25-4.33(1H, m), 7.67(1H, dd, J=8.1 Hz, J=12.6 Hz), 8.68(1H, s), 11.64(1H, s), 14.71(1H, br.). MS(m/z): 282(M$^+$+1).

Embodiment 2

Preparation of Ethyl 1-cyclopropyl-6,7-difluoro-8-hydroxyl-1,4-dihydro-4-oxoquinoline-3-carboxylate The preparation comprises refluxing a mixture of 1-cyclopropyl-6,7-difluoro-8-hydrohyl-4-oxoquinoline-3-carboxylic acid (target product of embodiment 1, 20.0 g, 71.2 mmol), concentrated sulfuric acid (5 mL) and ethanol (300 mL) to give a clear solution, cooling down to room temperature, filtering, washing obtained filter cake with ethanol, and drying to give 1-cyclopropyl-6,7-difluoro-8-hydroxy-1,4-dihydro-4-oxoquinoline-3-carboxylate (20.9 g, 95.0%).

$^1$H NMR(CDCl$_3$) δ=0.85-1.11(4H, m), 1.42(3H, t, J=6.9 Hz), 4.33-4.40(1H, m), 4.42(2H, q, J=6.9 Hz), 7.80-7.85(1H, m), 8.68(1H, s). MS(m/z): 310(M$^+$+1)

Embodiment 3

Preparation of Ethyl 1-cyclopropyl-6,7-difluoro-8-difluoromethoxyl-1,4-dihydro-4-oxoquinoline-3-carboxylate The preparation comprises mixing 1-cyclopropyl-6,7-difluoro-8-hydroxyl-1,4-dihydro-4-oxoquinoline-3-carboxylate (target product of embodiment 2, 5.0 g, 16.2 mmol), NaOH (1.3 g, 32.4 mmol), and water (0.5 mL) with chlorodifluoromethane (25.0 g) dissolved in N,N-dimethyl formamide (100 mL) in a 250 mL autoclave, reacting for 6 h at 100° C., cooling to room temperature, charging the reaction mixture into water (500 mL), stirring, filtering, and drying obtained filter cake to give ethyl 1-cyclopropyl-6,7-difluoro-8-difluoromethoxyl-1,4-dihydro-4-oxoquinoline-3-carboxylate (3.8 g, 65.4%).

$^1$H NMR(CDCl$_3$) δ=1.03-1.30(4H, m), 1.39(3H, t, J=6.9 Hz), 3.95-4.00(1H, m), 4.38(2H, q, J=6.9 Hz), 6.97(1H, t, J=72.9 Hz), 8.21(1H, t, J=9.6 Hz), 8.62(1H, s). MS(m/z): 360(M$^+$+1).

Embodiment 4

Preparation of ethyl 1-cyclopropyl-6,7-difluoro-8-difluoromethoxyl-5-nitro-1,4-dihydro-4-oxoquinoline-3-carboxylate The preparation comprises dissolving ethyl 1-cyclopropyl-6,7-difluoro-8-difluoromethoxyl-1,4-dihydro-4-oxoquinoline-3-carboxylate (target product of embodiment 3, 1.0 g, 2.8 mmol) in concentrated sulfuric acid (10 mL), slowly adding potassium nitrate (2.0 g, 19.8 mmol), reacting for 1 h at 40° C., cooling down to room temperature, charging the reaction mixture into ice water (100 mL), stirring, filtering, treating obtained filter cake with ethanol (20 mL), refluxing for 0.5 h, cooling down to room temperature, filtering, and drying obtained filter cake to give ethyl 1-cyclopropyl-6,7-difluoro-8-difluoromethoxyl-5-nitro-1,4-dihydro-4-oxoquinoline-3-carboxylate (0.5 g, 45.5%).

$^1$H NMR(DMSO) δ=0.99-1.11(4H, m), 1.22(3H, t, J=7.0 Hz), 3.88-3.92(1H, m), 4.18(2H, q, J=7.0 Hz), 7.24(1H, t, J=72.0 Hz), 8.56(1H, s). MS(m/z): 405(M$^+$+1).

Embodiment 5

Preparation of [1S,6S]-8-benzyl-2-tertbutyloxycarbonyl-2,8-diazabicyclo[4,3,0]nonane The preparation comprises stirring [1S,6S]-8-benzyl-2,8-diazabicyclo[4,3,0]nonane (5.0 g, 23.1 mmol) in methanol (50 mL) at room temperature, adding batchwise tertbutyloxycarbonyl dicarbonate (5.1 g, 23.4 mmol), stirring for 0.5 h, vacuum distilling to remove solvent, and column chromatographing with petroleum ether and ethyl, acetate at the ratio of 10:1 to give [1S,6S]-8-benzyl-2-tertbutyloxycarbonyl-2,8-diazabicyclo[4,3,0]nonane (7.1 g, 97.2%), $[α]^{20}_D$=−72.4° (CHCl$_3$, C=5).

$^1$H NMR(CDCl$_3$) δ=1.50(9H, s), 1.56-1.73(4H, m), 2.12 (1H, br.), 2.53-2.78(5H, m), 3.62-3.72(2H, m), 3.86(1H, br.), 4.56(1H, br.), 7.23-7.32(5H, m). MS(m/z): 317(M$^+$+1).

Embodiment 6

Preparation of [1R,6R]-8-benzyl-2-tertbutyloxycarbonyl-2,8-diazabicyclo[4,3,0]nonane As is in embodiment 5, [1R,6R]-8-benzyl-2-tertbutyloxycarbonyl-2,8-diazabicyclo[4,3,0]nonane is obtained by reacting [1R,6R]-8-benzyl-2,8-diazabicyclo[4,3,0]nonane with tertbutyloxycarbonyl dicarbonate, $[α]^{20}_D$=+71.8° (CHCl$_3$, C=5).

$^1$H NMR(CDCl$_3$) δ=1.50(9H, s), 1.57-1.73(4H, m), 2.14 (1H, br.), 2.54-2.78(5H, m), 3.62-3.73(2H, m), 3.86(1H, br.), 4.57(1H, br.), 7.23-7.35(5H, m). MS(m/z): 317(M$^+$+1).

Embodiment 7

Preparation of cis-8-benzyl-2-tertbutyloxycarbonyl-2,8-diazabicyclo[4,3,0]nonane As is in embodiment 5, cis-8-benzyl-2-tertbutyloxycarbonyl-2,8-diazabicyclo[4,3,0]nonane is obtained by reacting cis-8-benzyl-2,8-diazabicyclo[4,3,0]nonane with tertbutyloxycarbonyl dicarbonate.

$^1$NMR(CDCl$_3$) δ 1.50(9H, s), 1.55-1.73(4H, m), 2.12(1H, br.), 2.53-2.79(5H, m), 3.65-3.74(2H, m), 3.84(1H, br.), 4.55 (1H, br.), 7.23-7.35(5H, m). MS(m/z): 317(M$^+$+1).

Embodiment 8

Preparation of cis-8-benzyl-2-acetyl-2,8-diazabicyclo[4,3,0]nonane

The preparation comprises dissolving cis-8-benzyl-2,8-diazabicyclo[4,3,0]nonane (5.0 g, 23.1 mmol) in dichloromethane (50 mL) and triethylamine (5 mL) under stirring in ice bath, dropwise adding a solution of acetyl chloride (1.8 g, 23.1 mmol) in chloroform (10 mL), continuing with the stirring until the reaction finishes, distilling off the solvent, and chromatographing on silica gel with petroleum ether and ethyl acetate to give cis-8-benzyl-2-acetyl-2,8-diazabicyclo [4,3,0]nonane (5.1 g, 85.5%).

$^1$H NMR(CDCl$_3$) δ 1.68-1.85(4H, m), 1.98(3H, s), 2.21 (1H, br.), 2.58-2.87(5H, m), 3.68-3.73(2H, m), 3.87(1H, br.), 4.58(1H, br.), 7.23-7.36(5H, m). MS(m/z): 259(M$^+$+1).

Embodiment 9

Preparation of [1S,6S]-2-tertbutyloxycarbonyl-2,8-diazabicyclo[4,3,0]nonane

The preparation comprises dissolving [1S,6S]-8-benzyl-2-tertbutyloxycarbonyl-2,8-diazabicyclo[4,3,0]nonane (target product of Embodiment 5, 5.0 g, 15.8 mmol) in methanol (50 mL), adding 10% Pd/C (1.0 g) as catalyst for hydrogenation under 3 atm for 10 h, filtering to remove the catalyst, concentrating the filtrate, adding petroleum ether to solidify the product, filtering, and drying obtained filter cake to give [1S,6S]-2-tertbutyloxycarbonyl-2,8-diazabicyclo[4,3,0]nonane (3.1 g, 86.8%), $[α]^{20}_D$=−70.2° (C=4).

$^1$H NMR(CDCl$_3$) δ=1.45(9H, s), 1.66-1.70(2H, m), 2.03-2.11(2H, m), 2.72-2.88(2H, m), 3.11-3.78(5H, m), 3.92-3.97 (1H, m), 4.53-4.55(1H, m). MS(m/z): 227(M$^+$+1).

Embodiment 10

Preparation of [1R,6R]-2-tertbutyloxycarbonyl-2,8-diazabicyclo[4,3,0]nonane

[1R,6R]-8-benzyl-2-tertbutyloxycarbonyl-2,8-diazabicyclo[4,3,0]nonane (target product of embodiment 6) is catalytically hydrogenated according to the procedure similar to embodiment 9 to give [1R,6R]-2-tertbutyloxycarbonyl-2,8-diazabicyclo[4,3,0]nonane, $[α]^{20}_D$=+84.1° (C=4).

$^1$H NMR(CDCl$_3$) δ=1.45(9H, s), 1.66-1.71(2H, m), 2.03-2.11(2H, m), 2.71-2.89(2H, m), 3.10-3.77(5H, m), 3.92-3.99 (1H, m), 4.53-4.56(1H, m). MS(m/z): 227(M$^+$+1).

Embodiment 11

Preparation of cis-2-tertbutyloxycarbonyl-2,8-diazabicyclo[4,3,0]nonane cis-8-Benzyl-2-tertbutyloxycarbonyl-2,8-diazabicyclo[4,3,0]nonane (target product of embodiment 7) is catalytically hydrogenated according to the procedure similar to embodiment 9 to give cis-2-tertbutyloxycarbonyl-2,8-diazabicyclo [4,3,0]nonane.

$^1$H NMR(CDCl$_3$) δ=1.45(9H, s), 1.66-1.71(2H, m), 2.03-2.13(2H, m), 2.70-2.87(2H, m), 3.11-3.79(5H, m), 3.92-3.99 (1H, m), 4.50-4.55(1H, m). MS(m/z):227(M$^+$+1).

Embodiment 12

Preparation of cis-2-acetyl-2,8-diazabicyclo[4,3,0]nonane cis-8-Benzyl-2-acetyl-2,8-diazabicyclo[4,3,0]nonane (embodiment 8 compound) is catalytically hydrogenated according to the procedure similar to embodiment 9 to give cis-2-acetyl-2,8-diazabicyclo[4,3,0]nonane.

$^1$H NMR(CDCl$_3$) δ=1.64-1.70(2H, m), 2.01(3H, s), 2.01-2.11(2H, m), 2.70-2.88(2H, m), 3.08-3.78(5H, m), 3.90-3.99 (1H, m), 4.50-4.57(1H, m). MS(m/z): 169(M$^+$+1).

Embodiment 13

Preparation of 1-cyclopropyl-8-difluoromethoxyl-7-[(1S,6S)-2,8-diazabicyclo[4,3,0]nonane-8-yl]-6-fluoro-1,4-dihydro-4-oxoquinoline-3-carboxylic acid hydrochloride The preparation comprises reacting boric acid (1.1 g, 17.8 mmol) with acetic anhydride (6 mL, 62.5 mmol) at 110° C. for 1.5 h, cooling, adding glacial acetic acid (7.1 mL) to further react at 110° C. for 1 h, naturally cooling to 50-60° C., adding ethyl 1-cyclopropyl-6,7-difluoro-8-difluoromethoxyl-1,4-dihydro-4-oxoquinoline-3-carboxylate (target product embodiment 3, 4.3 g, 12.0 mmol), stirring for 6 h, vacuum distilling to remove solvent, charging into ice water (150 mL), stirring for 0.5 h, filtering, washing obtained filter cake with water and ethanol in turn, drying to give a white solid (5.1 g), reacting the obtained white solid (0.5 g, 1.1 mmol) with [1S,6S]-2-tertbutyloxycarbonyl-2,8-diazabicyclo[4,3,0]nonane (target product of embodiment 9, 0.7 g, 3.1 mmol) in pyridine (20 mL) as solvent at room temperature for 2 h under stirring, distilling off the solvent to give a residue (0.6 g), adding acetyl chloride (5 mL) slowly into methanol (10 mL) under ice-cooling, stirring for 30 min at room temperature to prepare a solution of methanol/methyl acetate in anhydrous HCl, adding the aforementioned residue (0.6 g) dissolved in methanol (5 mL), stirring for 0.5 h at room temperature, distilling to remove solvent, adding ethylether (50 mL) to solidify the product, filtering, and subjecting obtained filter cake to recrystallization with ethanol to give 1-cyclopropyl-8-difluoromethoxyl-7-[(1S,6S)-2,8-diazabicyclo[4,3,0]nonane-8-yl]-6-fluoro-1,4-dihydro-4-oxoquinoline-3-carboxylic acid hydrochloride (0.4 g), $[α]^{22}_D$=−172.5°, (C=1). Calculated result (measured value) of element analysis for the product: C 53.23 (53.31), H 4.89 (4.78), N 8.87 (9.01), Cl 7.48 (7.49).

$^1$H NMR(CF$_3$COOD) δ=1.10-1.53(4H, m), 1.92-2.01(4H, m), 2.93(1H, br.), 3.21(1H, br.), 3.59-3.62(1H, m), 3.98-4.40 (6H, m), 6.47(1H, t, J=72.0 Hz), 8.04(1H, d, J=13.5 Hz), 9.24(1H, s). MS(m/z): 438(M$^+$+1).

The following salts can be likewise prepared, e.g. 1-cyclopropyl-8-difluoromethoxyl-7-[(1S,6S)-2,8-diazabicyclo[4,3,0]nonane-8-yl]-6-fluoro-1,4-dihydro-4-oxoquinoline-3-carboxylic acid hydrobromate 1-cyclopropyl-8-difluoromethoxyl-7-[(1S,6S)-2,8-diazabicyclo[4,3,0]nonane-8-yl]-6-fluoro-1,4-dihydro-4-oxoquinoline-3-carboxylic acid sulfate Embodiment 14

1-cyclopropyl-8-difluoromethoxyl-7-[(1R,6R)-2,8-diazabicyclo[4,3,0]nonane-8-yl]-6-fluoro-1,4-dihydro-4-oxoquinoline-3-carboxylic acid hydrochloride As is in embodiment 13, ethyl 1-cyclopropyl-6,7-difluoro-8-difluoromethoxyl-1,4-dihydro-4-oxoquinoline-3-carboxylate (product compound of embodiment 3) is treated with [1R,6R]-2-tertbutyloxycarbonyl-2,8-diazabicyclo[4,3,0]nonane (target product of embodiment 10) and then the amino-protecting group is removed with a solution of methanol/methyl acetate in anhydrous HCl to give the product, $[\alpha]^{22}_D=+169.5°$, (C=1).
$^1$H NMR(CF$_3$COOD) δ=1.08-1.49(4H, m), 1.90-2.00(4H, m), 2.91(1H, br.), 3.20(1H, br.), 3.57-3.60(1H, m), 3.97-4.41 (6H, m), 6.48(1H, t, J=72.1 Hz), 8.04(1H, d, J=13.5 Hz), 9.24(1H, s). MS(m/z): 438(M$^+$+1).

Embodiment 15

Preparation of 1-Cyclopropyl-8-difluoromethoxyl-7-[cis-2,8-diazabicyclo[4,3,0]nonane-8-yl]-6-fluoro-1,4-dihydro-4-oxoquinoline-3-carboxylic acid hydrochloride As is in embodiment 13, ethyl 1-cyclopropyl-6,7-difluoro-8-difluoromethoxyl-1,4-dihydro-4-oxoquinoline-3-carboxylic acid ester (target product of embodiment 3) is treated with cis-2-tertbutyloxycarbonyl-2,8-diazabicyclo[4,3,0]nonane (target product of embodiment 11) to give the product.
$^1$H NMR(CF$_3$COOD) δ=1.10-1.52(4H, m), 1.91-2.01(4H, m), 2.92(1H, br.), 3.22(1H, br.), 3.58-3.62(1H, m), 3.98-4.41 (6H, m), 6.48(1H, t, J=72.0 Hz), 8.04(1H, d, J=13.5 Hz), 9.24(1H, s). MS(m/z): 438(M$^+$+1).

Embodiment 16

Preparation of 1-Cyclopropyl-8-difluoromethoxyl-7-[cis-2,8-diazabicyclo[4,3,0]nonane-8-yl]-6-fluoro-1,4-dihydro-4-oxoquinoline-3-carboxylic acid Method 1 comprises neutralizing 1-cyclopropyl-8-difluoromethoxyl-7-[cis-2,8-diazabicyclo[4,3,0]nonane-8-yl]-6-fluoro-1,4-dihydro-4-oxoquinoline-3-carboxylic acid hydrochloride (target product of embodiment 15, 3.0 g) with ammonia water, refrigerating, filtering to obtain a solid, washing with cold water to give monohydrate of the product. MS(m/z): 438(M$^+$+1). Calculated result (measured value) of element analysis for the product: C 55.38(55.34), H 5.31 (5.45), N 9.23(9.25).
Method 2 comprises reacting boric acid (1.1 g,17.8 mmol) with acetic anhydride (6 mL, 62.5 mmol) for 1.5 h at 110° C., slightly cooling, adding acetic acid (7.1 mL) to further react for 1 h at 110° C., cooling to 50-60° C. naturally, adding ethyl 1-cyclopropyl-6,7-difluoro-8-difluoromethoxyl-1,4-dihydro-4-oxoquinoline-3-carboxylate (target product of embodiment 3, 4.3 g, 12.0 mmol), stirring for 6 h, vacuum distilling to remove solvent, charging into ice water (150 mL) under stirring, stirring for 0.5 h, filtering, washing obtained filter cake with water and ethanol in turn, drying to give a white solid (5.1 g), reacting the solid (0.5 g, 1.1 mmol) with cis-2-acetyl-2,8-diazabicyclo[4,3,0]nonane (product compound of embodiment 12, 0.5 g, 2.9 mmol) in pyridine (20 mL) as solvent, stirring to react for 2 h at room temperature, distilling to remove solvent, adding 15% NaOH (10 mL) and ethanol (10 mL), refluxing for 15 h, distilling to remove ethanol, cooling down to room temperature, adjusting pH to 10-11 with 30% acetic acid, filtering, adjusting pH of obtained filtrate to 7.0 with 30% acetic acid, stirring for 0.5 h, refrigerating, filtering, and washing obtained solid with cold water to give the title compound (0.36 g, 75.0%). The properties of the compound are the same as the product of method 1.

Embodiment 17

Preparation of 5-amino-1-cyclopropyl-8-difluoromethoxyl-7-[(1S,6S)-2,8-diazabicyclo[4,3,0]nonane-8-yl]-6-fluoro-1,4-dihydro-4-oxoquinoline-3-carboxylic acid hydrochloride The preparation comprises reacting 5-amino-1-cyclopropyl-6,7-difluoro-8-difluoromethoxyl-1,4-dihydro-4-oxoquinoline-3-carboxylic acid (compound of referential example 1, 0.50 g, 1.44 mmol) with [1S,6S]-2-tertbutyloxycarbonyl-2,8-diazabicyclo[4,3,0]nonane (target product of embodiment 9, 0.90 g, 3.98 mmol) in pyridine (20 mL) as solvent for 0.5 h at 100° C., distilling to remove solvent and obtain residue (0.73 g), adding acetyl chloride (5 mL) slowly into methanol (10 mL) under ice-cooling, stirring for 30 min to prepare a solution of methanol/methyl acetate in anhydrous HCl, adding a solution of aforementioned residue (0.73 g) in methanol (5 mL), stirring at room temperature, distilling to remove solvent, adding ethylether (50 mL) to solidify the product, filtering, and subjecting obtained filter cake to recrystallization with ethanol to give 5-amino-1-cyclopropyl-8-difluoromethoxyl-7-[(1S,6S)-2,8-diazabicyclo[4,3,0]nonane-8-yl]-6-fluoro-1,4-dihydro-4-oxoquinoline-3-carboxylic acid hydrochloride (0.45 g). $[\alpha]^{25}_D=-204.8°$ (DMSO, C=2).
$^1$H NMR(CDCl$_3$) δ=0.72-1.25(4H, m), 1.52-1.79(4H, m), 2.37(1H, br.), 2.68-2.71(1H, m), 3.05-3.09(1H, m), 3.38-3.44 (3H, m), 3.97-4.03(3H, m), 6.21(1H, t, J=72.9 Hz), 6.56(2H, br.), 8.65(1H, s). MS(m/z): 453(M$^+$+1).

Embodiment 18

Preparation of 5-Amino-1-cyclopropyl-8-difluoromethoxyl-7-[(1R,6R)-2,8-diazabicyclo[4,3,0]nonane-8-yl]-6-fluoro-1,4-dihydro-4-oxoquinoline-3-carboxylic acid hydrochloride As is in embodiment 17, 5-amino-1-cyclopropyl-6,7-difluoro-8-difluoromethoxyl-1,4-dihydro-4-oxoquinoline-3-carboxylic acid (referential example 1) compound is reacted with [1R,6R]-2-tertbutyloxycarbonyl-2,8-diazabicyclo[4,3,0]nonane (embodiment 9 compound) to give the title compound, $[\alpha]^{25}_D=+212.6°$ (DMSO, C=2).
$^1$H NMR(CDCl$_3$) δ=0.72-1.28(4H, m), 1.51-1.79(4H, m), 2.39(1H, br.), 2.68-2.73(1H, m), 3.06-3.11(1H, m), 3.38-3.42 (3H, m), 3.95-4.02(3H, m), 6.23(1H, t, J=72.9 Hz), 6.57(2H, br.), 8.65(1H, s). MS(m/z): 453(M$^+$+1).

Embodiment 19

Preparation of 5-Amino-1-cyclopropyl-8-difluoromethoxyl-7-(cis-2,8-diazabicyclo[4,3,0]nonane-8-yl)-6-fluoro-1,4-dihydro-4-oxoquinoline-3-carboxylic acid tri fluoroacetate As is in embodiment 17, 5-amino-1-cyclopropyl-6,7-difluoro-8-difluoromethoxyl-1,4-dihydro-4-oxoquinoline-3-carboxylic acid (target product of referential example 1) is reacted with cis-2-tertbutyloxycarbonyl-2,8-diazabicyclo[4,3,0]nonane (compound of embodiment 11). The amino-protecting group is removed with trifluoroacetic acid, instead of the solution of methanol/methyl acetate in anhydrous HCl, to give the target compound. Calculated results (measured values) of element analysis for the product: C 48.77(48.84), H 4.27(4.19), and N 9.89(10.01).
$^1$H NMR(CDCl$_3$) δ=0.71-1.26(4H, m), 1.53-1.78(4H, m), 2.37(1H, br.), 2.69-2.72(1H, m), 3.04-3.09(1H, m), 3.38-3.46 (3H, m), 3.99-4.06(3H, m), 6.20(1H, t, J=72.9 Hz), 6.55(2H, br.), 8.64(1H, s). MS(m/z): 453(M$^+$+1).

The following salts can be likewise prepared,
5-amino-1-cyclopropyl-8-difluoromethoxyl-7-(cis-2,8-diazabicyclo[4,3,0]nonane-8-yl)-6-fluoro-1,4-dihydro-4-oxoquinoline-3-carboxylic acid acetate;
5-amino-1-cyclopropyl-8-difluoromethoxyl-7-(cis-2,8-diazabicyclo[4,3,0]nonane-8-yl)-6-fluoro-1,4-dihydro-4-oxoquinoline-3-carboxylic acid lactate;
5-amino-1-cyclopropyl-8-difluoromethoxyl-7-(cis-2,8-diazabicyclo[4,3,0]nonane-8-yl)-6-fluoro-1,4-dihydro-4-oxoquinoline-3-carboxylic acid maleate;
5-amino-1-cyclopropyl-8-difluoromethoxyl-7-(cis-2,8-diazabicyclo[4,3,0]nonane-8-yl)-6-fluoro-1,4-dihydro-4-oxoquinoline-3-carboxylic acid oxalate.

Embodiment 20

Preparation of 5-Amino-1-cyclopropyl-8-difluoromethoxyl-7-(cis-2,8-diazabicyclo[4,3,0]nonane-8-yl)-6-fluoro-1,4-dihydro-4-oxoquinoline-3-carboxylic acid mesylate As is in embodiment 17, 5-amino-1-cyclopropyl-6,7-difluoro-8-difluoromethoxyl-1,4-dihydro-4-oxoquinoline-3-carboxylic acid (target product of referential example 1) is reacted with cis-2-tertbutyloxycarbonyl-2,8-diazabicyclo[4,3,0]nonane (target product of embodiment 11); then the amino-protecting group is removed by reacting with a solution of methylsulfonic acid in methanol, instead of the solution of methanol/methyl acetate in anhydrous HCl, to give the title compound. Calculated results (measured values) of element analysis for the product: C 48.17(48.20), H 4.96(5.12), and N 10.21(10.18).

The following salts can be likewise prepared, 5-amino-1-cyclopropyl-8-difluoromethoxyl-7-(cis-2,8-diazabicyclo[4,3,0]nonane-8-yl)-6-fluoro-1,4-dihydro-4-oxoquinoline-3-carboxylic acid p-toluene sulfonate.

Embodiment 21

Preparation of 5-Amino-1-cyclopropyl-8-difluoromethoxyl-7-(cis-2,8-diazabicyclo[4,3,0]nonane-8-yl)-6-fluoro-1,4-dihydro-4-oxoquinoline-3-carboxylic acid The preparation comprises neutralizing 5-amino-1-cyclopropyl-8-difluoromethoxyl-7-(cis-2,8-diazabicyclo[4,3,0]nonane-8-yl)-6-fluoro-1,4-dihydro-4-oxoquinoline-3-carboxylic acid trifluoroacetate (target product of embodiment 19, 3.0 g) with ammonia water, refrigerating, filtering, and washing obtained solid with cold water to give monohydrate of the title compound. MS(m/z):453(M$^+$+1). Calculated results (measured values) of element analysis for the product: C 53.62(53.58), H 5.36(5.48), and N 11.91(11.87).

Embodiment 22

The preparation of Coated Tablet

Core Ingredients

| | |
|---|---|
| Target compound of embodiment 13 | 10.0 g |
| Lactose | 50.0 g |
| Starch | 40.0 g |
| Hydroxypropyl cellulose | 4.0 g |
| 10% Polyvinylpyrrolidone in ethanol | qs |
| Magnesium stearate | 0.5 g |

The aforementioned ingredients are mixed uniformly, pelletized, sieved, dried, and then tabletted into 100 core pieces.

Coating Liquid Ingredients

Opadry 5 g in 80% ethanol

Embodiment 23

Preparation of Capsule

Ingredients

| | |
|---|---|
| Target compound of embodiment 14 | 100 g |
| Starch | 10 g |
| Sodium carboxymethylcellulose | 20 g |
| Low-substituted hydroxypropyl cellulose | 10 g |
| Tween 80 | qs |
| 5% Polyvinylpyrrolidone in ethanol | qs |
| Sodium laurylsulfate | 8 g |
| 0# capsule dissolvable in stomach | 1,000 pieces |

The above ingredients are made into 1,000 pieces of capsules.

Preparation Method

The method comprises respectively sieving prescription amount of materials, adding 5% polyvinylpyrrolidone alcohol solution and Tween 80, sieving with 20 mesh sieve, air drying at room temperature around 15° C., mixing with sodium laurylsulfate, loading into 0# capsule dissolvable in stomach in the amount of 0.27 g/S, sampling, and assaying, wherein the dissolution Limit Q=80%, and the content should be 90-110% of the labeled value.

Embodiment 24

Preparation of Injection

The preparation comprises dissolving target compound of embodiment 17 1 g in appropriate amount of water for injection, adding poloxamer 10 g, sodium chloride 4 g, dextran 10 g, glucose 4 g and mannitol 5 g, mixing, adding water for injection to 1,000 mL, and preparing into 10 vials of intravenous injection.

The invention claimed is:

1. A quinolonecarboxylic acid derivative of formula (I), or a pharmaceutically acceptable salt or hydrate thereof,

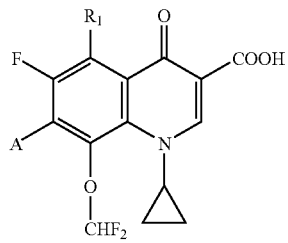

wherein $R_1$ is a hydrogen atom or an amino group, A has a structure of formula (II) with (1S,6S) configuration, a structure of formula (III) with (1R,6R) configuration, or a structure of formula (IV) with cis-racemic configuration,

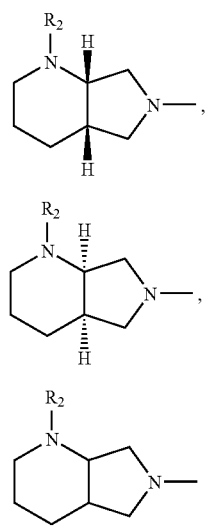

in which $R_2$ is a hydrogen atom or an amino-protecting group.

2. The quinolonecarboxylic acid derivative, pharmaceutically acceptable salt or hydrate thereof according to claim 1, wherein the amino-protecting group is formyl, acetyl, trifluoroacetyl, benzoyl, paranitrobenzoyl, p-toluene sulfonyl, methoxycarbonyl, ethoxycarbonyl, fluorenyl methoxycarbonyl, t-butyl-oxycarbonyl (BOC) or trichloroethoxycarbonyl.

3. The quinolonecarboxylic acid derivative, pharmaceutically acceptable salt or hydrate thereof according to claim 1, wherein the quinolonecarboxylic acid derivative is a pharmaceutically acceptable salt of an inorganic acid or an organic acid.

4. The quinolonecarboxylic acid derivative, pharmaceutically acceptable salt or hydrate thereof according to claim 3, wherein the quinolonecarboxylic acid derivative is a salt of hydrochloric acid, hydrobromic acid, phosphoric acid or sulfuric acid.

5. The quinolonecarboxylic acid derivative, pharmaceutically acceptable salt or hydrate thereof according to claim 3, wherein the quinolonecarboxylic acid derivative is a salt of methanesulfonic acid, paratoluenesulfonic acid, acetic acid, trifluoroacetic acid, lactic acid, citric acid, maleic acid, oxalic acid, succinic acid, benzoic acid, tartaric acid, fumaric acid, mandelic acid, ascorbic acid or malic acid.

6. A pharmaceutical composition comprising a quinolonecarboxylic acid derivative according to claim 1, or a pharmaceutically acceptable salt or hydrate thereof, wherein the pharmaceutical composition comprises a physiologically effective quantity of at least one quinolonecarboxylic acid derivative admixed with at least one pharmaceutically acceptable carrier.

7. The pharmaceutical composition of claim 6, wherein the composition is in the form of a tablet, sugar-coated tablet, film-coated tablet, enteric coating tablet, slow release tablet, capsule, hard capsule, soft capsule, slow release capsule, oral liquid, mistura, buccal tablet, granule, pill, pulvis, concentrated extract, bolus, suspension, liquor, injection, powder and injection preparation, freeze drying powder and injection preparation, powder, dispersible powder, cachet, suppositorium, ointment, plaster, cream, spray, aerosol, gutt, or patch.

8. The pharmaceutical composition of claim 7, wherein the composition is a solid or semisolid pharmaceutical preparation in the form of powder, tablet, dispersible powder, capsule, cachet, suppositorium or ointment, and the composition further comprises a solid carrier.

9. The pharmaceutical composition of claim 8, wherein the solid carrier is selected from diluent, flavoring agent, solubilizing agent, lubricant, suspending agent, binder, and swelling agent, or it can be coating material.

10. The pharmaceutical composition of claim 9, wherein the solid carrier is selected from one or more of magnesium carbonate, magnesium stearate, talcum, sucrose, lactose, pectin, dextrin, starch, gelatin, tragacanth, methyl cellulose, sodium carboxymethylcellulose, low boiling point wax, and cocoa butter.

11. A method to treat a bacterial infection, said method comprising administering an effective amount of a quinolonecarboxylic acid derivative of formula (I),

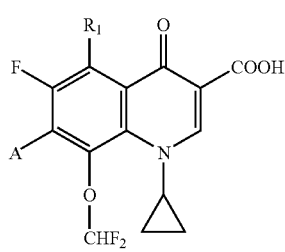

wherein $R_1$ is a hydrogen atom or an amino group, and
A has a structure of formula (II) with (1S,6S) configuration, a structure of formula (III) with (1R,6R) configuration, or a structure of formula (IV) with cis-racemic configuration,

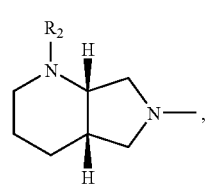

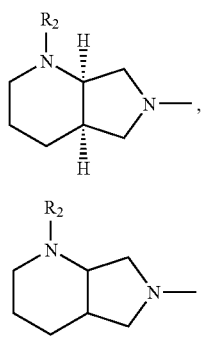

in which R₂ is a hydrogen atom or an amino-protecting group,
or a pharmaceutically acceptable salt or hydrate thereof.

12. The method of claim 11, wherein the quinolonecarboxylic acid derivative is a pharmaceutically acceptable salt of an inorganic acid or an organic acid.

13. The pharmaceutical composition of claim 6, wherein the quinolonecarboxylic acid derivative is a pharmaceutically acceptable salt of an inorganic acid or an organic acid.

14. The pharmaceutical composition of claim 13, wherein A has the formula (II) with (1S,6S) configuration.

15. The pharmaceutical composition of claim 13, wherein A has the formula (III) with (1R,6R) configuration.

16. The pharmaceutical composition of claim 13, wherein A has the formula (IV) with cis-racemic configuration.

17. The quinolonecarboxylic acid derivative of claim 3, wherein A has the formula (II) with (1S,6S) configuration.

18. The quinolonecarboxylic acid derivative of claim 3, wherein A has the formula (III) with (1R,6R) configuration.

19. The quinolonecarboxylic acid derivative of claim 3, wherein A has the formula (IV) with cis-racemic configuration.

20. The quinolonecarboxylic acid derivative of claim 1, which is selected from the group consisting of:
1-cyclopropyl-8-difluoromethoxyl-7-[(1S,6S)-2,8-diazabicyclo[4,3,0]nonane-8-yl]-6-fluoro-1,4-dihydro-4-oxoquinoline-3-carboxylic acid hydrochloride;
1-cyclopropyl-8-difluoromethoxyl-7-[(1S,6S)-2,8-diazabicyclo[4,3,0]nonane-8-yl]-6-fluoro-1,4-dihydro-4-oxoquinoline-3-carboxylic acid hydrobromate;
1-cyclopropyl-8-difluoromethoxyl-7-[(1S,6S)-2,8-diazabicyclo[4,3,0]nonane-8-yl]-6-fluoro-1,4-dihydro-4-oxoquinoline-3-carboxylic acid sulfate;
1-cyclopropyl-8-difluoromethoxyl-7-[(1R,6R)-2,8-diazabicyclo[4,3,0]nonane-8-yl]-6-fluoro-1,4-dihydro-4-oxoquinoline-3-carboxylic acid hydrochloride;
1-Cyclopropyl-8-difluoromethoxyl-7-[cis-2,8-diazabicyclo[4,3,0]nonane-8-yl]-6-fluoro-1,4-dihydro-4-oxoquinoline-3-carboxylic acid hydrochloride;
1-Cyclopropyl-8-difluoromethoxyl-7-[cis-2,8-diazabicyclo[4,3,0]nonane-8-yl]-6-fluoro-1,4-dihydro-4-oxoquinoline-3-carboxylic acid;
5-amino-1-cyclopropyl-8-difluoromethoxyl-7-[(1S,6S)-2,8-diazabicyclo[4,3,0]nonane-8-yl]-6-fluoro-1,4-dihydro-4-oxoquinoline-3-carboxylic acid hydrochloride;
5-Amino-1-cyclopropyl-8-difluoromethoxyl-7-[(1R,6R)-2,8-diazabicyclo[4,3,0]nonane-8-yl]-6-fluoro-1,4-dihydro-4-oxoquinoline-3-carboxylic acid hydrochloride;
5-Amino-1-cyclopropyl-8-difluoromethoxyl-7-(cis-2,8-diazabicyclo[4,3,0]nonane-8-yl)-6-fluoro-1,4-dihydro-4-oxoquinoline-3-carboxylic acid trifluoroacetate;
5-amino-1-cyclopropyl-8-difluoromethoxyl-7-(cis-2,8-diazabicyclo[4,3,0]nonane-8-yl)-6-fluoro-1,4-dihydro-4-oxoquinoline-3-carboxylic acid acetate;
5-amino-1-cyclopropyl-8-difluoromethoxyl-7-(cis-2,8-diazabicyclo[4,3,0]nonane-8-yl)-6-fluoro-1,4-dihydro-4-oxoquinoline-3-carboxylic acid lactate;
5-amino-1-cyclopropyl-8-difluoromethoxyl-7-(cis-2,8-diazabicyclo[4,3,0]nonane-8-yl)-6-fluoro-1,4-dihydro-4-oxoquinoline-3-carboxylic acid maleate;
5-amino-1-cyclopropyl-8-difluoromethoxyl-7-(cis-2,8-diazabicyclo[4,3,0]nonane-8-yl)-6-fluoro-1,4-dihydro-4-oxoquinoline-3-carboxylic acid oxalate;
Preparation of 5-Amino-1-cyclopropyl-8-difluoromethoxyl-7-(cis-2,8-diazabicyclo[4,3,0]nonane-8-yl)-6-fluoro-1,4-dihydro-4-oxoquinoline-3-carboxylic acid mesylate;
5-amino-1-cyclopropyl-8-difluoromethoxyl-7-(cis-2,8-diazabicyclo[4,3,0]nonane-8-yl)-6-fluoro-1,4-dihydro-4-oxoquinoline-3-carboxylic acid p-toluene sulfonate; and
5-Amino-1-cyclopropyl-8-difluoromethoxyl-7-(cis-2,8-diazabicyclo[4,3,0]nonane-8-yl)-6-fluoro-1,4-dihydro-4-oxoquinoline-3-carboxylic acid.

* * * * *

UNITED STATES PATENT AND TRADEMARK OFFICE
CERTIFICATE OF CORRECTION

| | |
|---|---|
| PATENT NO. | : 7,759,362 B2 |
| APPLICATION NO. | : 11/578828 |
| DATED | : July 20, 2010 |
| INVENTOR(S) | : Huiyuan Guo et al. |

It is certified that error appears in the above-identified patent and that said Letters Patent is hereby corrected as shown below:

In the Specification:

In column 3, line 35, change "200° C." to --200° C--, therefor.

In column 3, line 63, change "0-130° C." to --0-130° C--, therefor.

In column 4, line 18, change "pound (VII)" to --pound (VIII)--, therefor.

In column 5, line 25, change "200° C." to --200° C--, therefor.

In column 5, line 42, change "200° C." to --200° C--, therefor.

In column 5, line 67, change "0-130° C." to --0-130° C--, therefor.

In column 6, line 60, change "0-120° C." to --0-120° C--, therefor.

In column 7, line 55, change "10-100° C." to --10-100° C--, therefor.

In column 7, line 56, change "-50° C. to -10° C." to -- -50° C to -10° C--, therefor.

In column 7, line 57, change "5 atm" to --5atm--, therefor.

In column 8, line 11, change "wt %" to --wt%--, therefor.

In column 8, line 12, change "wt %" to --wt%--, therefor.

In column 9, TABLE 1, immediately below "Gram-negative bacteria", change "0.051" in the charts numbered Compd. 17 to --0.015--, therefor.

In column 11, line 14, change "100° C." to --100° C--, therefor.

In column 11, line 34, change "100° C." to --100° C--, therefor.

In column 12, line 5, change "100° C." to --100° C--, therefor.

In column 12, line 28, change "40° C." to --40° C--, therefor.

In column 12, line 50, change "ethyl,acetate" to --ethyl acetate--, therefor.

In column 12, line 66, change "+$^{71.80°}$" to --+71.80°--, therefor.

In column 14, line 38, change "110° C." to --110° C--, therefor.

Signed and Sealed this
Twenty-first Day of June, 2011

David J. Kappos
*Director of the United States Patent and Trademark Office*

CERTIFICATE OF CORRECTION (continued)
U.S. Pat. No. 7,759,362 B2

In column 17, line 6, change "tri fluoroacetate" to --trifluoroacetate--, therefor.

In column 17, line 57, change "sul fonate" to --sulfonate--, therefor.

In the Claims:

In column 22, line 36, claim 20, delete "Preparation of".